United States Patent [19]

Takashima

[11] Patent Number: 5,249,467
[45] Date of Patent: Oct. 5, 1993

[54] PRESSURE DETECTING APPARATUS

[75] Inventor: Mitsuru Takashima, Tokyo, Japan

[73] Assignee: Sony Corporation, Japan

[21] Appl. No.: 744,267

[22] Filed: Aug. 13, 1991

[30] Foreign Application Priority Data

Aug. 20, 1990 [JP] Japan .................. 2-217227
Mar. 18, 1991 [JP] Japan .................. 3-077264

[51] Int. Cl.$^5$ .............................................. G01L 11/00
[52] U.S. Cl. ........................................ 73/702; 128/672
[58] Field of Search .......... 73/702, 715, 7.05, 862.41; 128/672, 675

[56] References Cited

U.S. PATENT DOCUMENTS

| | | | |
|---|---|---|---|
| 3,503,263 | 3/1970 | Intraub | 73/702 |
| 3,868,954 | 3/1975 | Ueda | 128/687 |
| 4,066,066 | 1/1978 | Hee Soo Paek | 128/689 |

FOREIGN PATENT DOCUMENTS

0386619 9/1990 European Pat. Off. .
1150177 6/1963 Fed. Rep. of Germany .

*Primary Examiner*—Donald O. Woodiel
*Attorney, Agent, or Firm*—Ronald P. Kananen

[57] ABSTRACT

A pressure detecting apparatus comprises a pressure sensor having a vibrating element forming a pressure sensing surface, which is secured to a housing at the periphery thereof; and a pressure transmission member including an abutment portion having an abutment surface which is in contact with a position to be detected and a transmission portion projecting from the substantial center of the rear side of the abutment portion. The transmission member has the tip end surface area which is smaller than that of the pressure sensing surface of said pressure sensor. The transmission portion is secured to the substantial center of the pressure sensing surface of the said pressure sensor at the tip end surface thereof. The area of the abutment surface of said abutment portion being larger than that of the tip end surface of said transmission portion whereby said transmission member being adapted to transmit the pressure applied upon the abutment surface of said abutment portion to the pressure sensing surface of said pressure sensor via the tip end surface of said transmission portion.

9 Claims, 3 Drawing Sheets

PRESSURE DETECTING APPARATUS

BACKGROUND OF THE INVENTION

1. FIELD OF THE INVENTION

The present invention relates to a contact type pressure detecting apparatus and a pressure propagating speed detecting apparatus to which the pressure detecting apparatus is applied.

2. RELATED ART

A pressure detecting apparatus (hereinafter referred to as a pressure sensor) used in, for example, an apparatus for sphygmic diagnosis based upon vascular pulses in oriental medicine is adapted to directly bias the artery for detecting the arterial pulses.

The sphygmic diagnosis in the oriental medicine will be briefly described.

In the oriental medicine, the conditions of a patient are determined by sphygmic diagnosis solely relying on the sense of touch of the arterial pulses on the "sunko", that is, the processus styloideus radii in the inner side of the wrist. In the sphygmic diagnosis of the oriental medicine, the pulses on the "sunko" are classified into those on three spots, such as upper, middle and lower spots which are referred to as "shun", "khan" and "shaku", respectively and two kinds of pulsation condition "myakki" on the pulse route "keimyaku" appeared on respective spots are sensed.

The term "shun" means the distal end side of the artery of the wrist. The pulses on the "shun" represent the health conditions of a patient from the head to the chest. The term "khan" means the middle artery of the wrist between the distal end and the heart. The pulses on the "khan" represents the health conditions between the chest and the navel. The term "shaku" means the heart side of the artery in the wrist and the pulses on the "shaku" represents the health conditions between the navel and the toe.

A sphygmic diagnosis apparatus in which arterial pulses are detected from the artery of a human being by means of sensors such as infra-red ray sensor or pressure sensor for performing the diagnosis by observation of the sphygmogram has heretofore been known as is disclosed in the specification of the Japanese Examined Patent Publication No. 57-52054.

The disclosed diagnosis apparatus comprises three pressure sensors 51, 52 and 53 for converting the arterial pulses on the three spots such as "shun" "khan" and "shaku" of the "sunko" into electrical signal waves and a cuff band 55 which is mounted on the wrist 54 of a patient for biasing the pressure sensors 51, 52 and 53 upon the artery of the wrist as shown in FIG. 4.

The pressure sensors 51, 52 and 53 are disposed on the wrist 54, that is, on and along the artery in the "sunko" and the cuff 55 is wrapped around the wrist. A compressed air is pumped into an air bag (not shown) provided on the cuff 55 from a pneumatic pump via a conduit 56. The arterial pulses can be measured by adjusting the amount of the pumped air to change the pressure applied upon the artery. The pressure sensors 51, 52 and 53 are connected with an electromagnetic oscillograph and the like through connection codes 51, 52 and 53, respectively so that the measured arterial pulses are recorded on a recording paper and the like for observing the sphygmogram.

The pressure sensors 51, 52 and 53 comprises, for example, so-called electrostatic microphones or piezoelectric microphones. Specifically, in case of the electrostatic microphone, a high d.c. voltage is applied across an electrode of a vibrating plate and a fixed electrode via a resistor of several tens MΩ. The electrode of the vibrating plate is brought into direct contact with a spot on which a pressure is detected, for example the artery of the "sunko". The spacing between the electrode of the vibrating plate and the fixed electrode is changed due to pressure to change the electrostatic capacity therebetween. The voltage generated at this time is detected.

The pressure sensing surface of the pressure sensor used for, for example, the sphygmic diagnosis apparatus requires an enough rigidity since the vibrating plate electrode upon which pressure is applied, that is, the pressure sensing surface is biased toward the artery. Such a pressure sensor will be hereinafter referred to as a contact type pressure sensor. Accordingly, the contact type pressure sensor 60 is formed so that a pressure sensing surface 61 forms a part of a housing as shown in, for example, FIG. 5B. The contact type pressure sensor 60 thus has a sensitivity distribution in which the sensitivity is the highest in the center of the pressure sensing surface 61 and decreases in a direction toward the outer periphery thereof.

Therefore, when the pressure on the artery of the "sunko" which is smaller than the pressure sensing surface of the contact type pressure sensor, if the pressure sensing surface of the contact type pressure sensor is differently positioned relative to the spot to be detected, a largely different error is resulted so that reproducibility of measuring is not good.

A method of measuring the speed of a fluid flowing through a tube having an elasticity, for example, the speed of blood flowing through the artery and the pressure propagating speed may include two contact type pressure sensors biased toward the artery for determining the speed based upon the distance between the pressure sensors and the pressure propagating time (speed=distance/time).

In this case, it is necessary to adjust the areas of the pressure sensing surfaces of the pressure sensors depending upon the speed of the fluid to be measured. For example, the wave form of the pressure detected by the pressure sensor is changed so that the half value width becomes narrower as the peak value increases when the speed of the fluid is high and the half value width becomes wider as the peak value decreases when the speed of the fluid is low. It is necessary to detect the pressure at a small area of the pressure detecting surface (hereinafter referred to as pin point) when the speed is low like a blood flow. However, the pin point detection has a problem that the detection sensitivity is low. On the other hand, the area of the pressure sensing surface can be made wider when the speed of the fluid is fast. A problem will occur in the detection accuracy if the detection distribution of the pressure sensing surface is not uniform as mentioned above.

The present invention was made under such circumstances.

It is a first object of the present invention to provide a pressure detecting apparatus which can obtain a uniform sensitivity distribution even if a contact type pressure sensor has a pressure sensing surface in which sensitivity distribution is ununiform.

It is a second object to provide a pressure propagating speed detecting apparatus which can precisely measure the speed and pressure propagating speed of a fluid flow such as blood flow having a low speed and can freely adjust the detection sensitivity.

SUMMARY OF THE INVENTION

In order to accomplish the first object, the present invention provides a pressure detecting apparatus, comprising; a pressure sensor having a vibrating element forming a pressure sensing surface, which is secured to a housing at the periphery thereof; and a pressure transmission member including an abutment portion having an abutment surface which is in contact with a position to be detected and a transmission portion projecting from the substantial center of the rear side of the abutment portion; said transmission member having the tip end surface area which is smaller than that of the pressure sensing surface of said pressure sensor, said transmission portion being secured to the substantial center of the pressure sensing surface of the said pressure sensor at the tip end surface thereof; the area of the abutment surface of said abutment portion being larger than that of the tip end surface of said transmission portion whereby said transmission member being adapted to transmit the pressure applied upon the abutment surface of said abutment portion to the pressure sensing surface of said pressure sensor via the tip end surface of said transmission portion.

In order to accomplish the second object, the present invention provides a pressure propagating speed detecting apparatus, comprising; first and second pressure detecting means, each including a pressure sensor having a vibrating element forming a pressure sensing surface, which is secured to a housing at the periphery thereof; and a pressure transmission member including an abutment portion having an abutment surface which is in contact with a position to be detected and a transmission portion projecting from the substantial center of the rear side of the abutment portion;

said transmission member having the tip end surface area which is smaller than that of the pressure sensing surface of said pressure sensor, said transmission portion being secured to the substantial center of the pressure sensing surface of the said pressure sensor at the tip end surface thereof; the area of the abutment surface of said abutment portion being larger than that of the tip end surface of said transmission portion whereby said transmission member being adapted to transmit the pressure applied upon the abutment surface of said abutment portion to the pressure sensing surface of said pressure sensor via the tip end surface of said transmission portion; and means for determining the pressure propagating speed based upon the time difference between the detection outputs from said first and second pressure detecting means and the distance between said first and second pressure detecting means.

In the pressure detecting apparatus of the present invention, the transmission member transmits the pressure applied upon the abutment surface of the abutment portion to a position of the pressure sensing surface of the pressure sensor to which the tip end surface of the transmission portion is secured.

In the pressure propagating speed detecting apparatus of the present invention, the pressure propagating speed is calculated based upon the time difference measured by means of the first and second pressure detecting apparatuses and the distance between the first and second pressure detecting apparatuses.

DESCRIPTION OF THE EMBODIMENT

Figure 1:
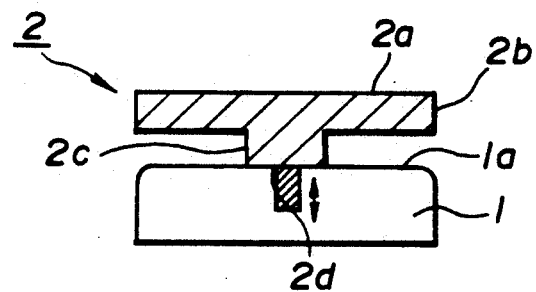
FIG. 1 is a partial sectional view of an embodiment of a pressure detecting apparatus of the present invention.

Now, an embodiment of a pressure detecting apparatus of the present invention will be described with reference to drawings. FIG. 1 is a partial sectional view of a pressure detecting apparatus.

The pressure detecting apparatus comprises a pressure sensor 1 which is an electrostatic microphone (so called capacitor microphone) and an attachment 2 secured to a pressure sensing surface 1a of the pressure sensor 1 as shown in FIG. 1.

The pressure sensor 1 is a contact type pressure sensor having a vibration plate electrode which is directly biased as the pressure sensing surface 1a toward the artery for detecting, for example, the arterial pulses of so called sunko (radius). The pressure sensor 1 is secured to a housing (not shown) at the periphery of the pressure sensing surface 1a. Accordingly, the pressure sensor 1 has such a sensitivity distribution that the sensitivity is highest in the center of the pressure sensing surface 1a and is lowered in a radial direction toward the periphery thereof.

Figure 2:
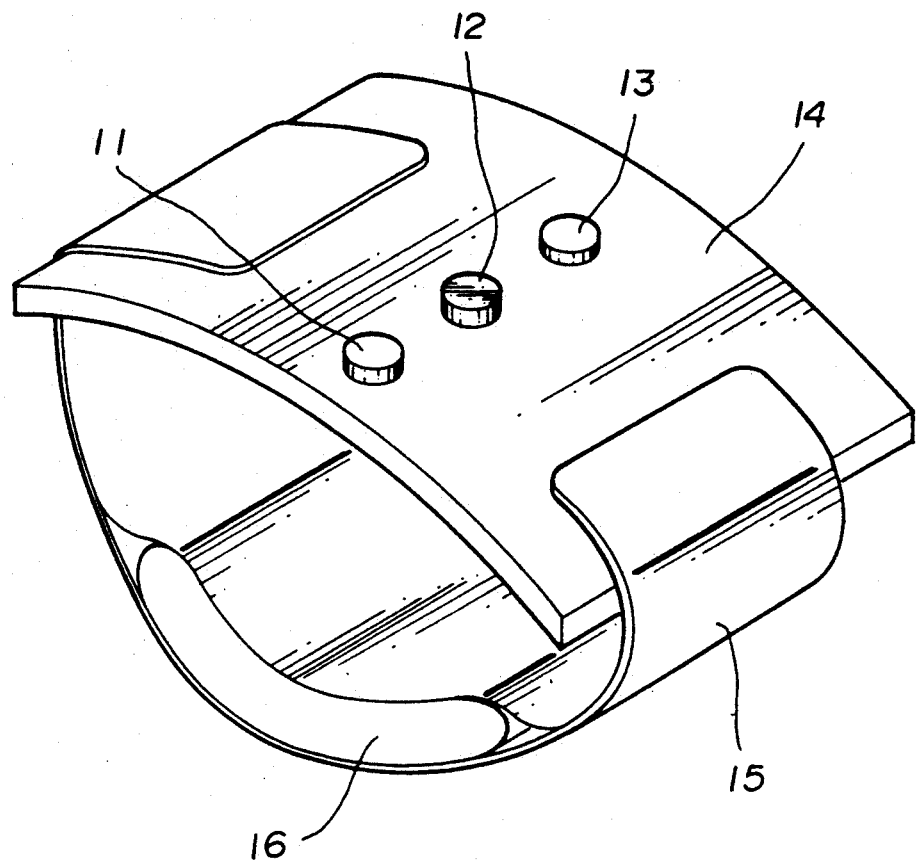
FIG. 2 is a schematic perspective view showing a pulse detecting apparatus which uses the pressure detecting apparatus of the present invention.
Figure 4:
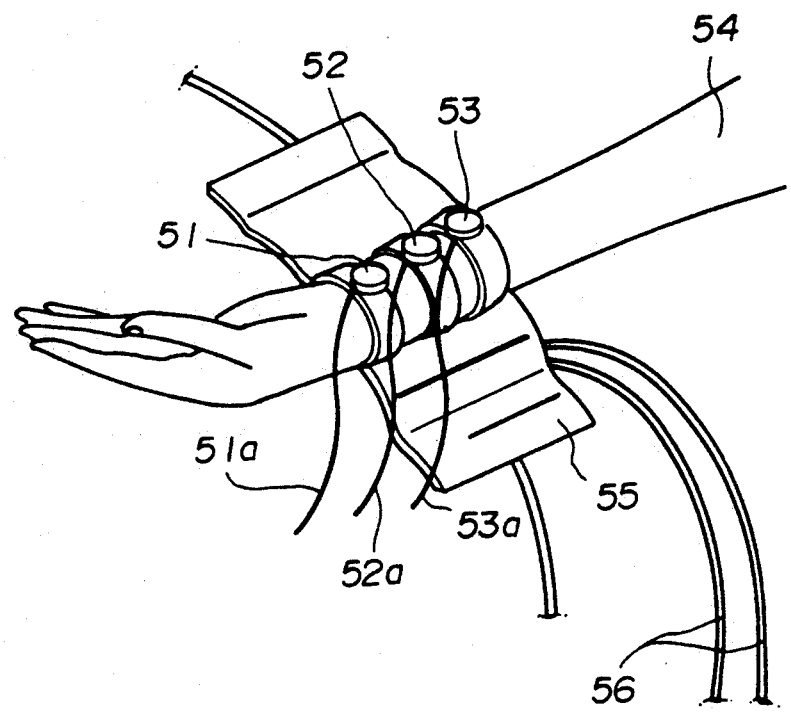
FIG. 4 is a schematic perspective view showing a prior art pulse detecting apparatus.

The attachment 2 comprises a disc-like abutment portion 2b having an abutment surface 2a which will be in contact with a position to be detected and a cylindrical transmission portion 2c projecting from the rear side of the abutment portion 2b in the substantial center thereof as shown in FIG. 2. The section of the attachment is T-shaped. The area of the tip end surface 2d of the transmission portion 2c is smaller than that of the pressure sensing surface 1a of the pressure sensor 1. The area of the abutment surface 2a of the aburment portion 2b is larger than that of the tip end surface 2d of the transmission portion 2c. The attachment 2 is secured to the substantial center of the pressure sensing surface 1a of the pressure sensor 1 at the tip end surface 2d of the transmission portion 2c. The attachment 2 is adapted to transmit the pressure applied upon the abutment surface 2a of the abutment portion 2b to the pressure sensing surface 1a of the pressure sensor 1 via the tip end surface 2d of the transmission portion 2c.

In the thus formed pressure detecting apparatus, the pressures applied to any positions of the abutment surface 2a of the attachment 2 are transmitted to the position of the pressure sensing surface 1a of the pressure sensor 1 to which the attachment 2 is secured. Accordingly, the sensitivity distribution of the abutment surface 2a becomes uniform. In other words, an uniform sensitivity distribution can be obtained over the abutment surface 2a. A constant sensitivity can be obtained over the surface having a larger area by increasing the area of the abutment surface 2a.

The sensitivity can be changed or adjusted depending upon the sensitivity of the position of the pressure sensing surface 1a of the pressure sensor 1 to which the attachment 2 is secured by changing the area and the shape of the tip end surface 2d of the attachment 2.

The abutment portion 2b of the attachment 2 may be elliptical plate or rectangular plate which is suitable to the shape of the region to be detected. The abutment surface 2a is not limited to only flat and may be convexed or concaved depending upon the region to be detected, for example, the shape of the sunko.

A pulse detecting apparatus which uses the above mentioned pressure detecting apparatus (hereinafter referred to as pressure sensor) will now be described.

The pulse detecting apparatus is adapted to detect as changes in pressure, the arterial pulses in three spots such as "shun", "khan" and "shaku" of the "sunko" defined by the oriental medicine to obtain arterial pulse information and comprises three pressure sensors 11, 12 and 13 for detecting arterial pulses, a mounting plate 14 on which the pressure sensor 11, 12 and 13 are mounted, a cuff 15 is linked to the both ends of the mounting plate 14 so that the side of the plate on which the pressure sensors 11, 12 and 13 are mounted is located inside thereof, and an air bag 16 disposed on the cuff 15 so that the bag faces to the pressure sensors 11, 12, and 13 as shown in FIG. 2.

The three pressure sensors 11, 12 and 13 detect as changes in pressure the arterial pulses in three positions such as "shun", "khan" and "shaku" of the "sunko", respectively and comprise, for example, a piezoelectric microphone.

The mounting plate 14 has a cruvature in a direction of the artery of the carpus in position of the "sunko", the processus styloideus radii, which is larger than that in a vertical direction. The pressure sensor 11, 12 and 13 are disposed inside of the mounting plate 14 so that the sensors are positioned correspondingly on the three spots such as "shun", "khan", "shaku" of the "sunko", respectively. The mounting plate 14 is made of, for example, a transparent member having a rigidity so that the mounting positions of the pressure sensors 11, 12 and 13 are visually observed (by eyes) from the outside thereof.

The cuff 15 is linked to the mounting plate 14 at one end thereof by means of, for example, a bonding agent. On the other hand, the cuff 15 is detachably linked to the mounting plate 14 at the other end thereof by means of, for example, a Velcro tape so that a hand can be freely inserted between the mounting plate 14 and the air bag 16.

The air bag 16 is connected to a pneumatic pump (not shown) via a conduit as mentioned above and is adapted to press the back of the wrist to bias the pressure sensors 11, 12 and 13 upon the artery on three spots, such as "shun", "khan" and "shaku" of the "sunko" at a predetermined pressure.

In order to detect the pulses, a wrist is inserted between the mounting plate 14 and the air bag 16 and an air is pumped into the air bag 15, the positions of the pressure sensors 11, 12 and 13 relative to the artery positioned above the radius are visually observed through the mounting plate 14. The pressure sensors 11, 12 and 13 are biased toward the artery positioned above the radius so that they are exactly positioned thereon. Outputs from the pressure sensors 11, 12 and 13 are recorded in a signal wave form recording apparatus (not shown) such as electromagnetic oscillograph.

An accurate detection result can be normally obtained to provide a high reproducibility by forming the pressure sensors 11, 12 and 13 as shown in FIG. 1 in the thus formed pulse detecting apparatus provided that the abutment surfaces of the pressure sensors are positioned above the artery of the "sunko".

Figure 3:
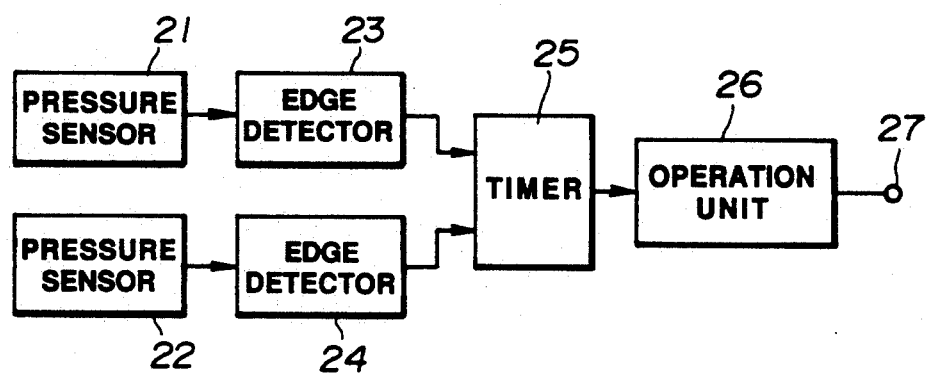
FIG. 3 is a block diagram showing the circuit structure of a pressure propagating speed detecting apparatus.
Figure 5:
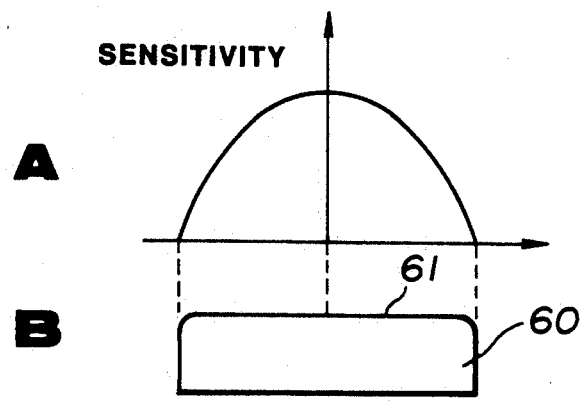
FIG. 5 is a view simultaneously showing the appearance of a pressure sensor and its sensitivity distribution.

An embodiment of a pressure propagating speed detecting apparatus using the pressure detecting apparatus of the present invention will be described. FIG. 3 is a block diagram showing the circuit structure of the pressure propagating speed detecting apparatus.

The pressure progagating speed detecting apparatus comprises two pressure sensors 21 and 22; edge detectors 23 and 24 for detecting, for example, the rise up edges of the outputs of the pressure sensors 21 and 22, respectively; a timer 25 for measuring the time difference between the rise up edges from the edge detectors 23 and 24; and an operational unit 26 for computing the fluid speed and the pressure transmitting speed based upon the time difference information from the timer 25 and the distance between the pressure sensors 21 and 22 as shown in FIG. 3. The pressure sensors 21 and 22 each comprises, for example, an electrostatic microphone having the attachment which has been described in the above-mentioned embodiment.

When the speed or the pressure propagation speed of a fluid flowing through a tube having an elasticity such as blood in the artery is measured, the pressure sensors 21 and 22 are separated apart with each other by a distance L and are biased upon the artery of the "sunko" and the outputs of the pressure sensors 21 and 22 are supplied to edge detecting circuit 23 and 24, respectively. The edge detectors 23 and 24 detect the rise up edges of the outputs of the pressure sensors 21 and 24, respectively and supply the results of the detection to the timer 25. The timer 25 measures the time difference T between the rise up edges and supplies the time difference T to the operational unit 26. The operational unit 26 computes the speed v of the blood flow in accordance with a formula represented below and outputs a result of computation from a terminal 27.

$$v = L/T$$

The speed and the pressure propagating speed can be more accurately detected by reducing the area of the abutment surfaces of the attachments of the pressure sensors 21 and 22 depending upon the speed of the blood flow, for example a low speed. The detection sensitivity can be freely adjusted by changing the area, shape and mounting position of the tip end surface of the attachment.

By using as pressure sensors 21 and 22, the pressure sensors of the above mentioned embodiment each having an abutment surface, the sensitivity distribution of which is uniform and is capable of freely adjusting the sensitivity and by adjusting the area of the abutment surface depending upon the speed of fluid, the speed of fluid and pressure propagating speed of the fluid, even the speed of slow fluid such as blood flow can be accurately measured. The detection sensitivity can be freely adjusted by changing the area, shape and mounting position of the tip end surfaces of the sensors.

As is apparent from the above description, the pressure detecting apparatus of the present invention has a transmission member comprising an abutment portion having an abutment surface which is in contact with a region to be detected and a transmitting portion projecting from the rear side of the abutment portion in the substantial center thereof. The area of the tip end surface of the transmitting portion is smaller than that of the pressure sensing surface of the pressure sensor. The area of the abutment surface of the abutment portion is larger than that of the tip end surface of the transmitting portion. The transmitting member has the transmitting portion at the tip end surface thereof secured to the substantial center of the pressure sensing surface of a pressure sensor having a vibration plate forming a pressure sensing surface for sensing a pressure secured to a housing at the periphery thereof. The pressure applied upon the abutment surface of the transmitting member is transmitted to the pressure sensing surface of the pressure sensor. Since the pressures applied to any positions of the abutment surface of the transmitting member are transmitted to the position of the pressure sensing surface of the pressure sensor, to which the transmitting member is secured, the sensitivity distribution of the abutment surface can be made uniform. In other words, an uniform sensitivity distribution can be obtained over an entire of the abutment surface. A constant sensitivity can be obtained at a larger area by increasing the area of, for example, the abutment surface.

The pressure propagating speed detecting apparatus uses first and second pressure detecting apparatus each comprising the pressure detecting apparatus to measure the time difference between the pressure detections achieved by the first and second pressure detecting apparatuses. The pressure propagating speed is computed based upon the measured time difference and the distance between the first and second pressure detecting apparatus. Even the speed and the pressure propagating speed of fluid flowing at a low speed such as blood can be accurately measured. The detection sensitivity can be freely adjusted by changing the area, shape and mounting position of the tip end surface of the pressure detecting apparatus.

What is claimed is:

1. A pressure detecting apparatus, comprising;
   a first pressure detecting means including:
      a pressure sensor having a vibrating element forming a pressure sensing surface, which is secured to a housing at the periphery thereof; and
      a pressure transmission member including an abutment portion having an abutment surface on a first side which is in contact with a source of pressure to be detected and a transmission portion projecting from the substantial center of a second side of the abutment portion;
      said transmission portion having a tip end surface with an area which is smaller than that of the pressure sensing surface of said pressure sensor, said transmission portion being secured to the substantial center of the pressure sensing surface of the said pressure sensor at the tip end surface thereof; the area of the abutment surface of said abutment portion being larger than that of the tip end surface of said transmission portion whereby said transmission member being adapted to transmit the pressure applied upon the abutment surface of said abutment portion to the pressure sensing surface of said pressure sensor via the tip end surface of said transmission portion.

2. A pressure detecting apparatus as defined in claim 1, further comprising;
   a second pressure detecting means having an abutment surface which is in contact with said source of pressure at a location spaced from said first pressure detecting means, and
   means for determining a pressure propagating speed based upon the time difference between the pressure detections made by said first and second pressure detecting means and the distance between said first and second pressure detecting means.

3. A pressure detecting apparatus as defined in claim 2 in which said means for determining the pressure propagating speed further comprises:
   means for measuring the time difference between the pressure detections made by said first and second pressure detecting means; and
   means for determining the pressure propagating speed based upon the time difference which has been measured by the time difference measuring means and the distance between said first and second pressure detecting means.

4. A pressure detecting apparatus as defined in claim 3 in which said time difference measuring means comprises means for detecting each edge of the output from said first and second pressure detecting means and means for detecting the time difference between the edges of the detection outputs from said first and second pressure detecting means.

5. A pressure detecting apparatus as defined in claim 2 in which said second pressure detecting means comprises:
   a pressure sensor having a vibrating element forming a pressure sensing surface, which is secured to a housing at the periphery thereof; and
   a pressure transmission member including an abutment portion having an abutment surface on a first side which is in contact with a source of pressure to be detected and a transmission portion projecting from the substantial center of a second side of the abutment portion;
   said transmission portion having a tip end surface with an area which is smaller than that of the pressure sensing surface of said pressure sensor, said transmission portion being secured to the substantial center of the pressure sensing surface of the said pressure sensor at the tip end surface thereof; the area of the abutment surface of said abutment portion being larger than that of the tip end surface of said transmission portion whereby said transmission member being adapted to transmit the pressure applied upon the abutment surface of said abutment portion to the pressure sensing surface of said pressure sensor via the tip end surface of said transmission portion.

6. A pressure detecting apparatus as defined in claim 1, further comprising:
   a second pressure detecting means;
   a mounting plate on which said first and second pressure detecting means are mounted; and
   a cuff means connected to opposite ends of the mounting plate for positioning said first and second pressure detecting means over the processus styloideus radii of a human wrist.

7. A pressure detecting apparatus as defined in claim 6, further comprising:
   a third pressure detecting means, said third detecting means also being mounted on said mounting plate for positioning over the processus styloideus radii of the wrist.

8. A pressure detecting apparatus as defined in claim 7, further comprising:
   an air bag disposed within the cuff means, said air bag adapted to press the back of the wrist for biasing said first, second and third pressure detecting means against the wrist.

9. A pressure detecting apparatus as defined in claim 7, wherein said first, second and third pressure detecting means are identical.

* * * * *